US00PP23582P3

(12) United States Plant Patent
Radler

(10) Patent No.: US PP23,582 P3
(45) Date of Patent: May 7, 2013

(54) FLORIBUNDA ROSE PLANT NAMED 'RADPROV'

(50) Latin Name: *Rosa hybrida*
Varietal Denomination: cv. Radprov

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/067,921

(22) Filed: Jul. 7, 2011

(65) Prior Publication Data

US 2013/0014297 P1 Jan. 10, 2013

(51) Int. Cl.
*A01H 5/00* (2006.01)

(52) U.S. Cl.
USPC ..... Plt./148

(58) Field of Classification Search ..... Plt./148, Plt./143, 141, 149
See application file for complete search history.

*Primary Examiner* — Kent L Bell
(74) *Attorney, Agent, or Firm* — Buchanan Ingersoll & Rooney

(57) ABSTRACT

A new and distinct Floribunda rose plant is provided that abundantly and substantially continuously forms attractive very double old-fashioned blossoms that are pink with undertones of lavender. The blossom fragrance is very strong and commonly is reminiscent of fresh citrus. The plant exhibits vigorous vegetation and an upright and bushy growth habit. The foliage is dark green with a semi-glossy finish. Good resistance to blackspot has been experienced. The plant is well suited for growing as attractive ornamentation in parks and gardens.

1 Drawing Sheet

Botanical/commercial classification: *Rosa hybrida*/Floribunda Rose Plant.

Varietal denomination: cv. Radprov.

SUMMARY OF THE INVENTION

The new variety of *Rosa hybrida* Floribunda rose plant of the present invention was created during 2003 at Greenfield, Wis., U.S.A., by artificial pollination wherein two parents were crossed which previously had been studied in the hope that they would contribute the desired characteristics. The female parent (i.e., the seed parent) was the 'Wekbipuhit' variety (U.S. Plant Pat. No. 11,513). The male parent (i.e., the pollen parent) of the new variety was the 'Radmis' variety (non-patented in the United States). The parentage of the new variety can be summarized as follows:

'Wekbipuhit'×'Radmis'.

The seeds resulting from the above pollination were sown and small plants were obtained which were physically and biologically different from each other. Selective study resulted in the identification of a single plant of the new variety.

It was found that the new Floribunda rose plant of the present invention possesses the following combination of characteristics:

(a) abundantly and substantially continuously forms attractive very double old-fashioned blossoms that are pink with undertones of lavender and display a strong fragrance,
(b) exhibits an upright and bushy growth habit,
(c) forms vigorous vegetation,
(d) forms attractive dark green foliage with a semi-glossy finish, and
(e) exhibits good resistance to blackspot.

A new rose variety is provided which bears fragrant old-fashioned pink blossoms combined with substantially continuous blooming and blackspot resistance.

The new variety well meets the needs of the horticultural industry. It can be grown to advantage as ornamentation in parks, gardens, public areas, and in residential settings. The new variety is particularly well suited for providing attractive ornamentation in the landscape. The pink blossoms contrast nicely with the semi-glossy dark green foliage.

The new variety of the present invention also can be readily distinguished from its ancestors. For instance, the 'Wekbipuhit' variety forms magenta-colored blossoms having a substantially lesser number of petals than the new variety. The 'Radmis' variety forms semi-double blossoms that are peach with tones of yellow and pink in coloration and displays a lower spreading growth habit. When the new variety is compared to the 'Meitripine' variety (U.S. Plant Pat. No. 22,318, granted Dec. 13, 2011), it is found that the 'Meitripine' variety forms lavender-colored blossoms also having a substantially lesser number of petals than the new variety.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radprov' and will be marketed in the United States under the ORCHID ROMANCE trademark.

BRIEF DESCRIPTION OF THE PHOTOGRAPH

The accompanying photograph shows, as nearly true as it is reasonably possible to make the same in a color illustration of this character, a typical specimen of the new variety. The illustrated rose plant of the new variety was approximately two years of age and was observed during June while growing outdoors on its own roots at West Grove, PA., U.S.A.

DETAILED DESCRIPTION

The chart used in the identification of colors is that of The Royal Horticultural Society (R.H.S. Colour Chart), London, England. The description is based on the observation of two-year-old specimens of the new variety during June while growing outdoors on their own roots at West Grove, Pa., U.S.A.

Class: Floribunda.

Plant:

*Height*.—Approximately 4.5 feet on average at the end of the growing season.

*Width*.—Approximately 3 feet on average at the end of one growing season.

*Habit*.—Upright and bushy.

Branches:

*Color*.—Young stems: near Green Group 137B. adult wood: near Yellow-Green Group 146B.

*Texture*.—Smooth on young branches and somewhat rough on adult branches.

*Thorns*.—Size: approximately 5 to 10 mm in length. color: when young near Greyed-Red Group 178A, and when mature near Greyed-Orange Group 164A.

Leaves:

*Size*.—A five-leaflet leaf commonly is approximately 13 cm in length on average and approximately 10.5 cm in width on average.

*Leaflets*.—Number. 3, 5, and 7. length: approximately 3 to 10 cm for a terminal leaflet, and approximately 2.5 to 7 cm for a lower leaflet. width: approximately 2 to 5 cm for a terminal leaflet, and approximately 1.5 to 4 cm for a lower leaflet. shape: ovate with a rounded base and an acuminate tip. margins: serrate. texture: smooth on both surfaces. overall appearance: attractive dark green semi-glossy foliage. color (young foliage): upper surface: Green Group 139A. under surface: Yellow-Green Group 147A. color (adult foliage): upper surface: Green Group 139A. under surface: Yellow-Green Group 147B with some Red-Purple Group 59B at the margins.

*Petioles*.—Length: commonly approximately 2 mm on average. diameter: commonly approximately 1 mm on average. texture: smooth. color: Yellow-Green Group 144A.

*Petiolules*.—Length: commonly approximately 2 mm on average. diameter: commonly approximately 1 mm on average. texture: smooth. color: Yellow-Green Group 144A overlaid with Red-Purple Group 61A.

*Stipules*.—Length: commonly approximately 1.7 cm on average. width: commonly approximately 1 mm on average. texture: smooth. color: Yellow-Green Group 144A.

Inflorescence:

*Number of flowers*.—Commonly approximately 15 blooms on average on a plant at a given time.

*Peduncle*.—Near Green Group 143A, commonly approximately 5 to 8 cm in length, smooth and covered with short flexible thorns having lengths of approximately 1 mm.

*Sepals*.—Number: five. shape: lanceolate. upper surface: canascent and near Green Group 138B in coloration. under surface: glabrous and near Green Group 138A in coloration. apex: aristulate. margin: entire. size: commonly approximately 3 to 3.5 cm in length on average and approximately 6 mm in width on average at the point of attachment.

*Buds*.—Shape: ovoid. length: approximately 2.5 to 3 cm on average. diameter: approximately 1 to 2 cm. color: near Red-Purple Group 60D.

*Flower*.—Form: very double. diameter: approximately 7 to 9 cm on average when fully open. height: commonly approximately 2.5 cm on average. color (when opening begins): upper surface: near Red-Purple Group 57C. under surface: near Red-Purple Group 57D. color (at end of blooming): upper surface: Purple Group 76A. under surface: Purple Group 76B. fragrance: very strong, and commonly is reminiscent of fresh citrus. petal number: commonly approximately 80 to 90 on average. petal apex: rounded and slightly mucronulate. petal shape: substantially rotund. petal length: commonly approximately 2.3 cm on average. petal width: commonly approximately 2.1 cm on average. petal margin: entire and slightly cupped inward. petal texture: glabrous on both surfaces. petal drop: good, with the petals commonly detaching freely and cleanly. stamen number: approximately 10 on average. anthers: approximately 3 mm in length, approximately 2 mm in width, and near Greyed-Orange Group 163A in coloration. filaments: commonly approximately 0.7 to 1 cm in length, and near Greyed-Orange Group 162D in coloration. pollen: commonly present in a sparse quantity and near Yellow-Orange Group 23A in coloration. pistils: separate and free, and commonly number approximately 35 on average. styles: commonly approximately 7 mm in length on average, and near Yellow-White Group 158C in coloration. stigmas: commonly approximately 1 mm in diameter on average, and near Yellow Group 11D in coloration. receptacle: oval in shape, smooth in texture, approximately 1.2 cm in length on average, approximately 8 mm in width on average, Yellow-Green Group 144A overlaid with Red-Purple Group 59B in coloration, and with achenes commonly being present on the bottom and wall.

Development:

*Vegetation*.—Vigorous and strong.

*Blossoming*.—Abundant and substantially continuous during the growing season.

*Resistance to diseases*.—Good with respect to blackspot, mildew, and rust.

*Hardiness*.—U.S.D.A. Hardiness Zone Nos. 6 to 9.

*Formation of hips/seeds*.—Sparse.

I claim:

1. A new and distinct Floribunda rose plant characterized by the following combination of characteristics:

(a) abundantly and substantially continuously forms attractive very double old-fashioned blossoms that are pink with undertones of lavender and display a strong fragrance, (b) exhibits an upright and bushy growth habit, (c) forms vigorous vegetation, (d) forms attractive dark green foliage with a semi-glossy finish, and (e) exhibits good resistance to blackspot;

substantially as herein shown and described.

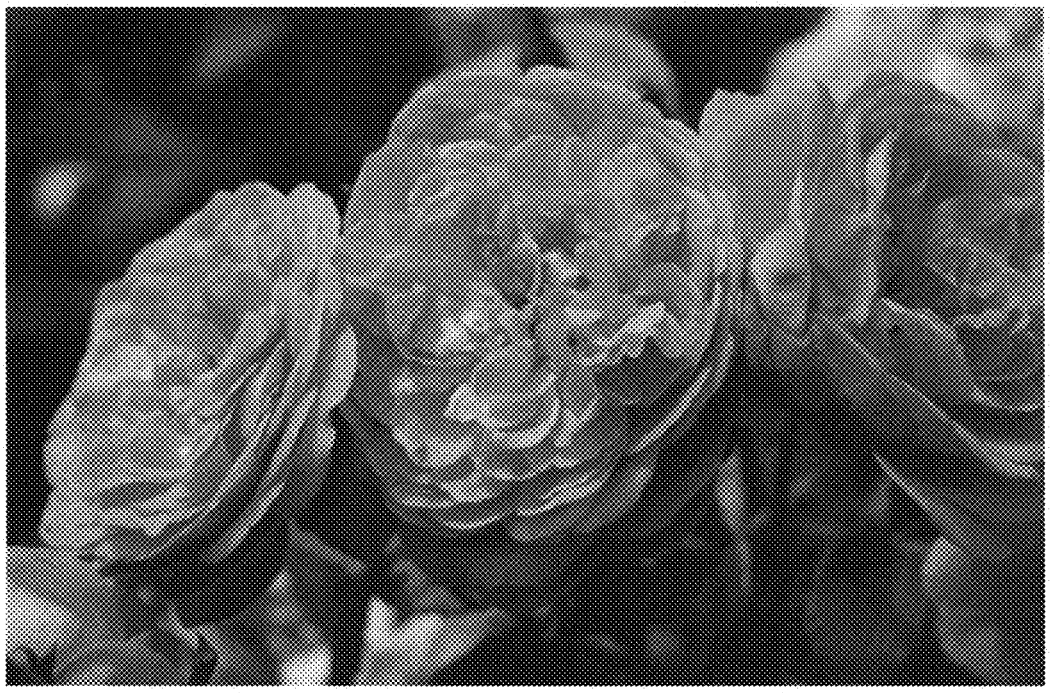

* * * * *